United States Patent [19]
Herrling

[11] 3,980,649
[45] Sept. 14, 1976

[54] PROCESS FOR THE MANUFACTURE OF PYRIMIDINE DERIVATIVES

[75] Inventor: Siegfried Herrling, Stolberg, Rhineland, Germany

[73] Assignee: Chemie Grunenthal GmbH, Stolberg, Rhineland, Germany

[22] Filed: Aug. 27, 1974

[21] Appl. No.: 500,960

[30] Foreign Application Priority Data
Aug. 29, 1973 Germany............................ 2343419

[52] U.S. Cl............................ 260/256.4 N; 424/251
[51] Int. Cl.²............... C07D 239/30; C07D 239/48
[58] Field of Search............................ 260/256.4 N

[56] References Cited
UNITED STATES PATENTS

| | | | |
|---|---|---|---|
| 2,433,440 | 12/1947 | Curd et al.................... | 260/256.4 N |
| 3,238,208 | 3/1966 | Gerns et al. ................. | 260/256.4 N |
| 3,455,923 | 1/1969 | Mizzoni et al. .............. | 260/256.4 N |
| 3,707,560 | 12/1972 | De Angelis et al. .......... | 260/256.4 N |

*Primary Examiner*—Nicholas S. Rizzo
*Assistant Examiner*—James H. Turnipseed
*Attorney, Agent, or Firm*—Weiser, Stapler & Spivak

[57] ABSTRACT

A process for the manufacture of 2,4-diamino-5-(substituted benzyl)pyrimidines from the corresponding 6-hydroxy-derivatives or the hydrochloride thereof by (a) chlorinating with phosphoryl chloride in presence of a considerable excess of hydrogen chloride and (b) hydrogenation of the thus easily in practically pure form and with high yields obtained 6-chloro derivatives.

9 Claims, No Drawings

PROCESS FOR THE MANUFACTURE OF PYRIMIDINE DERIVATIVES

The invention relates to a process for the manufacture of pyrimidine derivatives of the general formula I

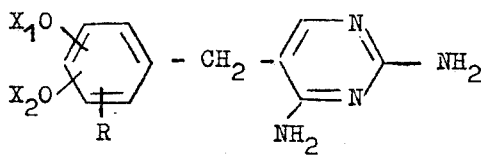

wherein $X_1$ and $X_2$ are the same or different alkyl radicals containing from one to three carbon atoms or together represent an alkylene radical containing one or two carbon atoms and wherein R represents a hydrogen atom or an alkoxy group containing one to three carbon atoms.

In a preferred form of the invention $X_1$ and $X_2$ each represent a methyl group and R represents a methoxy group.

Starting materials for the process of the invention are 6-hydroxy-pyrimidine derivatives of formula II

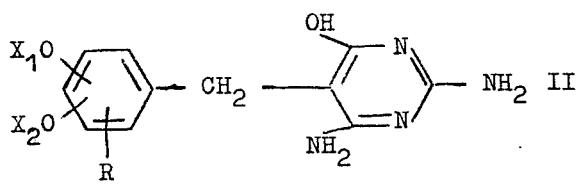

wherein $X_1$, $X_2$ and R have the same meaning as above.

Compounds of formula I are known to be valuable chemotherapeutics.

In the published German patent applications (DT-OS) Nos. 2 003 578, 2 165 362 and 2 258 238 the preparation of compounds of formula I starting with compounds of formula II has been claimed. On page 10 of DT-OS No. 2 258 238, however, it is pointed out (which statement has been confirmed by the results of own experiments) that the process of DT-OS No. 2 003 578 in several respects is not repeatable. First of all, it is impossible to react ethyl cyanoacetate with 3,4,5-trimethoxybenzylchloride under the conditions described in said publication. Also it is impossible to react 2,4-diamino-5-(3',4',5'-trimethoxybenzyl)-6-hydroxypyrimidine, (obtained by another process) in accordance with the description of "step C" on page 10 of DT-OS No. 2 003 578 to form 2,4-diamino-5-(3',4',5'-trimethoxybenzyl)-pyrimidine.

The process of example 15 of DT-OS No. 2 258 238 was repeatable but in several experiments the maximum yield obtained was less than 10 % which is far less than the figure given in that example (88 % of the theoretical yield are mentioned there).

Finally it was impossible to confirm the yield of 72 % said to be obtained in DT-OS No. 2 165 362, example 1, step C (pages 6 – 7). The maximum yield obtainable in repeating this procedure for several times was about 25 %.

The negative or poor, respectively, results described above obtained in following the published processes may be explained as follows: Brown and Mason in "The Pyrimidines" (1962), pages 163 – 164, point out that "conversion of hydroxy into chloro groups in the presence of amino groups is not always easy. On the whole, 2-amino groups are less troublesome than are 4- or 5-amino groups".

On page 928 of Houben-Weyl, *Methoden der organischen Chemie*, 4. Auflage Vol. 5/3 (1962) it is stated that by making use of a mixture of phosphoryl chloride and dimethylaniline it is also possible to convert the hydroxy group of hydroxy pyrimidines containing amino groups into a chloro atom. In case this method is applied to 2,4-diamino-6-hydroxypyrimidine, however, the yield is very poor (*J.Am.Chem.Soc.* 73 (1951) page 3011). Also experiments to make use of this method in the preparation of 6-chloro-2,4-diamino-5-(3',4',5'-trimethoxybenzyl)pyrimidine failed.

Surprisingly it has now been found that in compounds of formula II the 6-hydroxy group easily can be exchanged in high yields with a chloro atom by heating the compound of formula II or the hydrochloride thereof in phosphoryl chloride while passing continuously a stream of dry hydrogen chloride through the reaction mixture. In a preferred form of this process the reaction mixture is refluxed for several hours.

The success of the process of the invention is surprising in that it was unforeseeable that the chlorination of the amino substituted hydroxypyrimidine derivative of formula II (which with phosphoryl chloride or the mixture thereof with dimethylanilin proceeds at most with poor yields) can be easily performed in high yields in presence of a considerable excess of hydrogen chloride.

It is known that under the influence of acidic conditions especially in compounds containing 3,4,5-trimethoxyphenyl groups at least one of the methyl groups (liberating the 4-hydroxy group) easily is splitted off. Accordingly it is very surprising that in the process of the invention the two or three alkoxy groups contained in the compounds of formula II resist the reaction conditions.

In the process of the invention, the 6-chloropyrimidine derivatives of formula III

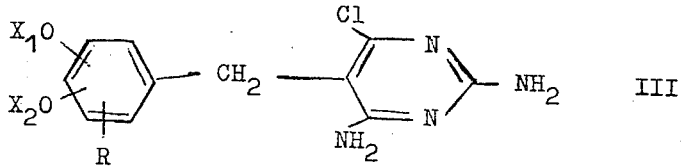

wherein $X_1$, $X_2$ and R have the same meaning as above are obtained from the reaction mixture by distilling off the remaining phosphoryl chloride, treatment of the residue with ice and hydrochloric acid and precipitation by alkalyzation in practically pure form. Therefore they can be submitted to the hydrogenolysis leading to compounds of formula I without intermediate measures (purification etc). Consequently also the compounds of formula I are obtained directly in practically pure form, so that isolation or purification steps, respectively, causing considerable losses are avoided.

The hydrogenolysis may be performed in the usual manner by treatment of the compound of formula II with hydrogen in presence of a palladium catalyst. In a preferred form of this hydrogenolyses the catalyst is palladized charcoal and the solvent is acetic acid containing 25 % of water and/or one to ten percent of sodium acetate, potassium acetate or the like.

The following non-limiting examples further illustrate the invention. All melting point values are uncorrected.

EXAMPLE 1 a. 10.2 g of 2,4-diamino-5-(3', 4', 5'-trimethoxybenzyl)-6-hydroxypyrimidine are suspended in 100 ml of absolute methanol. This suspension is cooled and saturated, while stirring, with dry hydrogen chloride. Thereby the product dissolves but on continued treatment with hydrogen chloride the hydrochloride of the pyrimidine derivative precipitates. The solvent is distilled off in a vacuum, the dry residue is pulverized.

b. The hydrochloride of 2,4-diamino-5-(3',4',5-trimethoxybenzyl)-6-hydroxypyrimidine thus obtained is introduced into 100 ml of freshly distilled phosphoryl chloride. A steady stream of dry hydrogen chloride is passed into the suspension which is refluxed for four hours. The resulting nearly colourless solution is freed off excess phosphoryl chloride by vacuum destillation. The residue is cooled and treated with about 50 g of ice followed by 45 ml of concentrated hydrochloric acid. The mixture becomes warm and a clear solution is formed, which is cooled again and then is introduced into an excess of ice-cooled aqueous ammonia while stirring.

The precipitate, which immediately is formed, is filtered off by suction, washed with water and dried. The raw material of 6-chloro-2,4-diamino-5-(3',4', 5'-trimethoxybenzyl)pyrimidine thus obtained melts at 216°–218°C. It is sufficient pure to be used in the next step. The yield is 9.5 g = 87.8 % of the theoretical yield.

c. 8.1 g of the product obtained in step (b) are dissolved in 100 ml of a mixture of 75 g of glacial acetic acid, 6 g of sodium acetate and 25 ml of water. 1 g of 5 % palladium on charcoal is added and then the mixture is hydrogenated by room temperature and normal pressure, until the absorption of hydrogen stops. The catalyst is removed and the filtrate is evaporated. The residue is dissolved in water, made alkaline with ammonia and extracted several times with chloroform. The combined extracts are washed with water, dried and evaporated to dryness. The residue is dissolved in the minimum amount of 10 % acetic acid and precipitated by treatment with aqueous ammonia. The 2,4-diamino-5-(3',4',5'-trimethoxybenzyl)-pyrimidine is filtered off, washed with water and dried. The yield is 5.6 g =77.3 % of the theoretical yield. The melting point is 197° – 198°C (uncorrected). The product was proven by thin-layer chromatography with several solvents to be uniform.

EXAMPLE 2 a. 10.2 g of 2,4-diamino-5-(3',4', 5'-trimethoxybenzyl)-6-hydroxypyrimidine are refluxed for 4 hours with 100 ml of freshly distilled phosphoryl chloride during which time a steady stream of dry hydrogen chloride is passed into the reaction mixture. The excess of phosphoryl chloride is removed by vacuum destillation. The residue is processed as described in Example 1b whereby crude 6-chloro-2,4-diamino-5(3',4',5'-trimethoxybenzyl)-pyrimidine melting at 215°–218°C is obtained in a yield of 7.7 g = 72.5 % of the theoretical yield.

b. 6.5 g of the material prepared in example 2a are dissolved in a mixture of 120 ml of glacial acetic acid and 4.5 g of sodium acetate, 5 % palladium on charcoal (1 g) is added and then the mixture is hydrogenated and further processed as described in Example 1c.

Thereby 2,4-diamino-5-(3',4',5'-trimethoxybenzyl)-pyrimidine is obtained in a yield of 4.1 g =70.7% of the theoretical yield. The product was proven by thin-layer chromatography to be uniform.

The same result was obtained in using 10 % palladium on charcoal as catalyst but otherwise proceeding as described above.

EXAMPLE 3

From 9.2 g of 2,4-diamino-5-(3',4'-dimethoxybenzyl)-6-hydroxypyrimidine the hydrochloride was prepared following the procedure described in Example 1a. This product was subjected to the process described in Example 1b whereby crude 6-chloro-2,4-diamino-5-(3',4'-dimethoxybenzyl)pyrimidine, melting at 218° – 220°C was obtained, which (without any previous purification) was hydrogenated and processed in the manner described in Example 1c. Thus 2,4-diamino-5-(3',-4'-dimethoxybenzyl)-pyrimidine, melting at 231° – 232°C was obtained.

What is claimed is:

1. The process for the manufacture of a pyrimidine derivative of formula I

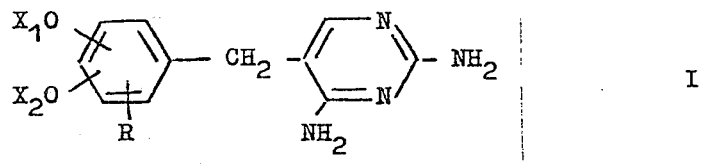

wherein $X_1$ and $X_2$ are the same or different alkyl of one to three carbons or together are alkylene of one or two carbons and wherein R is hydrogen or alkoxy of one to three carbons, which comprises the steps of reacting a compound of formula II

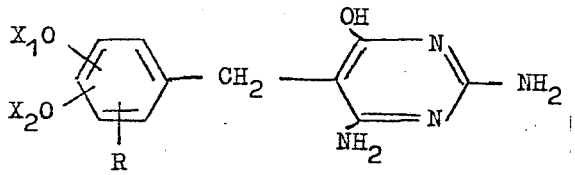
II or the hydrochloride thereof by heating with phosphoryl chloride while steadily passing into the reaction mixture a stream of dry hydrogen chloride to form the compound of formula III

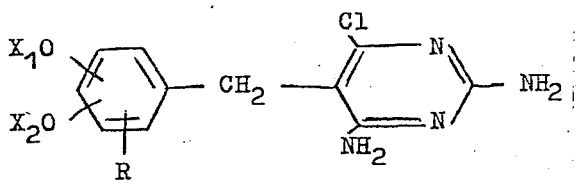
III which is isolated and subjected to a hydrogenolysis in presence of a palladium hydrogenation catalyst to form the compound of formula I.

2. Process according to claim 1, wherein $X_1$ and $X_2$ are methyl and R is methoxy.

3. Process according to claim 1 wherein the reaction mixture in the chlorinating step is refluxed for several hours.

4. Process according to claim 1 wherein the catalyst for the hydrogenolysis is palladized charcoal.

5. Process according to claim 1 wherein the solvent in the hydrogenolysis is a mixture of about 75% acetic acid and sodium acetate.

6. In the process for the manufacture of a 6-chloropyrimidine derivative of formula III of claim 1, wherein $X_1$ and $X_2$ are the same or different alkyl of one to three carbons and wherein R is hydrogen or alkoxy of one to three carbons, the improvement which comprises the steps of reacting a compound of formula II of claim 1, or the hydrochloride thereof, by heating it in the presence of phosphoryl chloride, under acidic conditions, while passing into the reaction mixture a steady stream of dry hydrogen chloride, thereby forming the 6-chloropyrimidine derivative of formula III of claim 1, and thereafter isolating it from the reaction mixture.

7. The process of claim 6 wherein the reaction is carried out by refluxing the compound of formula II with phosphoryl chloride.

8. The process of claim 6 wherein the chlorination of the compound of formula II is carried out while passing a steady stream of dry hydrogen chloride into the reaction mixture.

9. The process of claim 8 wherein the compound of formula II is chlorinated in the presence of an excess of hydrogen chloride.

* * * * *